United States Patent [19]

Giaever et al.

[11] Patent Number: 4,514,500

[45] Date of Patent: Apr. 30, 1985

[54] CELL GROWTH ON LIQUID-LIQUID INTERFACES

[75] Inventors: Ivar Giaever, Schenectady; Richard C. Keese, Schoharie, both of N.Y.

[73] Assignee: General Electric Company, Schenectady, N.Y.

[21] Appl. No.: 442,981

[22] Filed: Nov. 19, 1982

[51] Int. Cl.$^3$ .................... C12N 5/02; C12N 5/00; C12R 1/91

[52] U.S. Cl. .................... 435/241; 435/948; 435/240

[58] Field of Search .................... 435/240, 241, 948, 1, 435/2

[56] References Cited

U.S. PATENT DOCUMENTS 4,189,534 2/1980 Levine et al. .................... 435/2

FOREIGN PATENT DOCUMENTS 0085573 8/1983 European Pat. Off. ............ 435/241

OTHER PUBLICATIONS

M. D. Rosenberg, "The Culture of Cells and Tissues at the Saline–Fluorocarbon Interface"–*In: Tissue Culture,* (Proceedings of the Seminar held in Baroda under the auspices of the University Grants Commission and the Maharaja Sayajirao University of Baroda, India, Jan. 21-28, 1965, edited by C. V. Ramakrishnan, Dr. W. Junk, publishers, The Hague, 1965, pp. 93-107).
N. G. Maroudas, "Chemical and Mechanical Requirements for Fibroblast Adhesion", [*Nature,* vol. 244, (Aug. 10, 1973), pp. 353, 354].
M. D. Rosenberg, "Cell Surface Interactions and Interfacial Dynamics"-*In: Cellular Control Mechanism and Cancer,* [P. Emmelot and O. Muhlbock, pp. 146-163, (1964)].
W. L. McKeehan, et al., "Stimulation of Clonal Growth of Normal Fibroblasts with Substrata Coated with Basic Polymers", [*The Journal of Cell Biology,* vol. 71, (1976), pp. 727-734].
P. F. Davies, "Microcarrier Culture of Vascular Endothelial Cells on Solid Plastic Beads", [Experimental Cell Research 134, (1981), pp. 367-376].
D. W. Levine, et al., "Microcarrier Cell Culture: New Methods for Research–Scale Application", [*Somatic Cell Genetics,* vol. 3, No. 2, 1977, pp. 149-155].
"Cultivation of Living Cells on Liquid Perfluorocarbons", by Ivanitskii et al.; translated from Doklady Akademii Nauk SSSR, vol. 258, No. 1, pp. 225-228, May, 1981.

*Primary Examiner*—Thomas G. Wiseman
*Assistant Examiner*—John E. Tarcza
*Attorney, Agent, or Firm*—Leo I. MaLossi; James C. Davis, Jr.; James Magee, Jr.

[57] ABSTRACT

Droplets having an electrical charge on the surface thereof are prepared from a first liquid and dispersed in a second liquid, a sterile aqueous tissue culture medium containing serum proteins. The first liquid is non-toxic to living cells and is relatively immiscible with water. The electrical charge on the surfaces of the droplets has a charge density in the range of from about 10 to about 100 charges per square nanometer. Serum protein films adhere to the charged droplets strongly enough to prevent rupture by human fibroblast cells grown thereon.

12 Claims, 2 Drawing Figures

CELL GROWTH ON LIQUID-LIQUID INTERFACES

BACKGROUND OF THE INVENTION

This invention relates to tissue culture in which cells are grown in vitro in appropriate tissue culture media.

Various cell culture techniques including general laboratory instructions, cell propagation on various supports, counting of cell populations, the preparation of media reagents, etc. may be found in the *Handbook of Cell and Organ Culture*-Merchant, et al., Minneapolis, Burgess Publishing Company, 1964, Second Edition, and *Tissue Culture (Methods and Applications)* edited by P. F. Kruse, Jr. and M. F. Patterson, Jr., N.Y., Academic Press, 1973. In the commercial cultivation of cells, the cells grow as a monolayer on some sort of substrate, most commonly glass, or non-toxic plastic, in contact with tissue culture medium. Typically, the substrate may be the inner surface of a vessel containing the medium or may be the surface of small solid particles kept suspended in the medium. This latter mode of cell culture is also disclosed in "Microcarrier Culture of Vascular Endothelial Cells On Solid Plastic Beads" by P. F. Davies [*Experimental Cell Research* 134 (1981), pp. 367–376]. Several kinds of transformed cells will grow and divide in suspension in the tissue culture medium itself. The article "Microcarrier Cell Culture: New Methods for Research-Scale Application" by Levine, et al. [*Somatic Cell Genetics*, Vol. 3, No. 2, 1977, pp. 149–155] describes preparing hydrated beads of positive charge carrying dextran microspheres.

Still another method for cell and tissue culture which provides for the culture of cells at a liquid-liquid interface is described in the article by M. D. Rosenberg, "The Culture of Cells and Tissues at the Saline-Fluorocarbon Interface". *In: Tissue Culture* (Proceedings of the Seminar held in Baroda under the auspices of the University Grants Commission and the Maharaja Sayajirao University of Baroda, India, Jan. 21–28, 1965 edited by C. V. Ramakrishnan, Dr. W. Junk, publishers, the Hague, 1965, pp. 93–107). The cell culture system described by Rosenberg consists of a lower fluorocarbon liquid phase and an upper saline or nutrient liquid phase. The cells are grown in contact with the substantially planar interface between these two liquid phases. The use of silicone oils in place of the liquid fluorocarbons is also reported. This article by Rosenberg is incorporated by reference.

Further, it is reported in the article by N. G. Maroudas, "Chemical and Mechanical Requirements for Fibroblast Adhesion" [*Nature*, Vol. 244 (Aug. 10, 1973), pp. 353,354] that cells have been grown on the interface between medium and droplets of silicone oil.

The general process for growing cells on protein-coated droplets in an emulsion is described and claimed in U.S. patent application Ser. No. 443,311-Giaever and Keese, filed Nov. 23, 1982. Ser. No. 443,311 is a continuation-in-part of U.S. patent application Ser. No. 344,673-Giaever and Keese, filed Feb. 1, 1982.

DESCRIPTION OF THE INVENTION

In the general practice of this invention, cells are grown on a large number of small protein-coated droplets of a first liquid dispersed in a second liquid in the nature of an emulsion. One of these liquids is to be a sterile aqueous tissue culture medium and the other liquid, relatively immiscible with the tissue culture medium, is non-toxic to living cells. An emulsion is, typically, a heterogeneous system with at least one immiscible liquid dispersed in another in the form of droplets. The phase providing the droplets is the disperse, or internal, phase while the phase providing the matrix for the disperse phase is the continuous, or external phase.

In the practice of this invention liquid droplets of a disperse phase, typically a fluorocarbon, are introduced into an appropriate volume of sterile tissue culture medium containing serum proteins to make an emulsion. Before being brought into contact with this culture medium the droplets will have been provided with a surface active additive, dissolved therein which will result in an electrical charge on each droplet surface. The charge density should be high enough to securely bind serum proteins to the surfaces of the droplets but low enough so that the droplets do not stick together. A useful charge density range of from about 10 to about 100 charges/square nanometer results from the addition of from about 100 to about 1000 micrograms of the acid chloride pentafluorobenzoyl chloride (PFBC), respectively, per milliliter of pure fluorocarbon when this mixture is converted to droplet form. The PFBC is surface active and becomes concentrated at the fluorocarbon-aqueous interface, where it is converted to pentafluorobenzoic acid. However, other polar substances compatible with (i.e. soluble in) a given disperse phase liquid can be used as the additive and the appropriate range of useful quantity for addition can be routinely determined using the criteria set forth above. Preferably the droplet surface charge density should be great enough that the adhesion of films of serum proteins thereto can resist rupture by growing human fibroblasts.

The emulsion is readily made by forcing the disperse phase into the tissue culture medium through a capillary. Vortexing or other means of agitation are other methods for distributing the disperse phase through the culture medium as many small droplets, however use of a capillary yields more uniformly sized droplets. The droplets should have sizes ranging from about 50 micrometers to about 400 micrometers and preferably from about 100 micrometers to about 250 micrometers. Droplet density should be in the range of from about 16,000 to about 1,000,000 droplets per cubic centimeter.

After initial introduction of the charged droplets, the container should be gently agitated to keep the droplets constantly in motion to promote coating by the protein. If there is a significant difference in the densities of the disperse and continuous phases, the system separates into two layers. In the case in which the non-toxic liquid (i.e. the disperse phase) selected is significantly heavier, the lower layer will comprise an emulsion rich in protein-coated droplets of the non-toxic liquid dispersed in tissue culture medium and the upper layer will be primarily excess tissue culture medium. Once properly coated with serum protein these droplets can be stored for months. Next, the system is inoculated with the cells to be grown and, thereafter, is maintained under conditions of temperature, pH, carbon dioxide concentration and oxygen tension so as to facilitate cell growth. After inoculation, the cells gradually settle through the liquid and reach the surface of the many small protein-coated droplets, where they adhere and grow as monolayers on the surfaces receiving their nutrient from the culture medium bathing the protein-coated droplets. During cell division, they change from a flat configuration adhering tightly to the protein surface covering the droplets to a more rounded configuration, in which condition they can readily move to unoccupied protein-covered droplets in order to grow there. Microscopic observation of the droplets with cells attached awash in the culture medium is greatly facilitated by using a transparent container.

After a period of at least 24 hours of growth time, or after whatever time is optimum for the cell/system combination, the harvesting of the cells is accomplished by simply breaking the emulsion (i.e. demulsification). This breaking of the emulsion is readily accomplished by spinning or centrifuging the system whereupon the disperse phase agglomerates; the two liquids separate creating a liquid-liquid interface; and, when the disperse phase is heavier than water, the cells go to the interface from which location they can be readily removed, as by the use of a pipette. Maximum yield is obtained by culturing the cells at 37° C., pH 7.2–7.3, the medium being equilibrated with 5% carbon dioxide in air and an oxygen tension of 50–100% air saturation.

The harvesting procedure in addition to the advantage of its simplicity also has the advantage that the use of chelating agents or enzyme solutions, such as trypsin, pancreatin or collagenase is obviated. Not only is a process step thereby eliminated, but in addition, the possible damage done to the cell surface by the enzymes is avoided.

Both the Merchant, et al. text and the Kruse, Jr., et al. text provide disclosure of the composition and preparation of many tissue culture media and various reagents employed in tissue culture. These texts are incorporated by reference. Many such media and media components are available commercially as are many cell line starter cultures. Various liquids useful as the disperse phase are disclosed in the Rosenberg article.

In the aforementioned Ser. No. 344,673, two modes for stiffening the protein layer on which cell growth is to occur are contemplated. In the first mode a film of polymeric material, which carries a positive (i.e. basic) charge at physiological pH, underlies the protein cell growth layer at the interface(s). In the second mode a cross-linking agent is permitted to react with the protein layer already at the interface(s). By the use of this invention (i.e. by the provision of droplets with sufficient electrical surface charge density) the layer of adsorbed serum protein is so firmly bound to the droplet surface, that there is no need to resort to "stiffening" mechanisms.

Replenishment of the culture medium to the growing cells may be accomplished by gentle rotation of the container and, although not employed in the examples described herein, positive circulation (i.e. perfusion) of fresh medium to the growing cells is contemplated within this invention.

BRIEF DESCRIPTION OF THE DRAWINGS

The features of this invention believed to be novel and unobvious over the prior art are set forth with particularity in the appended claims. The invention itself, however, as to the organization, method of operation and objects and advantages thereof, may best be understood by reference to the following description taken in conjunction with the accompanying drawing wherein:

MANNER AND PROCESS OF MAKING AND USING THE INVENTION

As is substantiated in the EXAMPLES set forth hereinafter, spreading and growth of normal human cells on the surfaces of droplets of disperse-phase liquids in emulsions with tissue culture medium have been demonstrated. This work has been done with fluorocarbon liquid droplets having negatively charged surface, because fluorocarbons are readily stabilized, separate well upon breaking of the emulsion and are reusable after sterilization. These fluorocarbons are characterized by lack of toxicity, inertness, high density (about 1.9), immiscibility with water, low solubility for most other materials, thermal and chemical stability, low viscosity, transparency (i.e. for microscopic viewing) and hydrophobicity.

In addition to using normal human cells, we expect that this invention is applicable to a variety of both primary and secondary cell lines.

Although experiments are only reported using PFBC as the additive, other surface active materials can be used. A second method can be used to generate the droplet surface charge, that is, by subjecting the disperse phase liquid to sonication in water or ethylene glycol and then separating the two phases by high speed centrifugation. In the case of fluorocarbons and water it is believed that locally high temperatures generated by the sonication bring about chemical reactions between the fluorocarbon and the water that produce polar compounds.

The preferred method for preparing the emulsion is to dissolve the desired amount of surface active additive in the fluorocarbon liquid to be used as the disperse phase and then to force the fluorocarbon through a capillary under a preset pressure into the serum-containing tissue culture medium to produce droplets about 200 microns in diameter. During injection of the fluorocarbon droplets in this manner the container for the tissue culture medium should be gently, continuously agitated keeping the culture medium in motion.

Although various standard tissue culture media having different quantities of serum can be used in the practice of this invention, the preferred culture medium is Dulbecco's modified Eagle's medium (DMEM) plus serum. Penicillin (100 units/ml) and streptomycin (100 micrograms/ml) were added to the DMEM as received.

Figure 1:
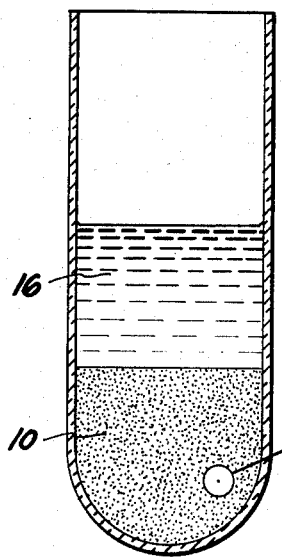
FIG. 1 is a schematic view in cross-section of an embodiment of this invention in which a container and its contents are employed for the growth of cells over the surface of droplets of the disperse phase.
Figure 2:
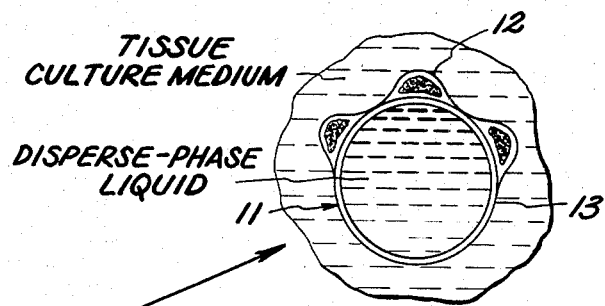
FIG. 2 is a schematic enlargement in cross-section showing living cells affixed to one of the protein-coated droplets of the disperse phase bathed in the tissue culture medium.

Inoculation of the emulsion with cells is accomplished by depositing the desired amount of cell suspension by pipette over the emulsion. The cells settle down through the liquid to contact the protein-coated droplets of disperse phase liquid in the emulsion (the lower layer 10 of material in FIG. 1). After sufficient incubation at 37° C. in a suitable atmosphere (95% air, 5% $CO_2$, 100% relative humidity), the cells spread out over the attached protein layer to each droplet 11, grow and increase in numbers. As shown schematically in FIG. 2, cells 12 attached to protein layer 13 grow over this outer surface area.

If extensive cell growth is desired, the medium can be partially refurbished by periodically drawing off spent medium from layer 16 and replacing it with fresh sterile medium. This cell culture operation could, of course, be carried out in an appropriate apparatus such that fresh medium could be supplied by perfusion.

When cell culture was conducted in a standard microtiter plate with cylindrical (7 mm diameter) wells, 0.1 ml of protein-coated disperse phase droplets plus culture medium (i.e. emulsion) was pipetted into the well. Next, 0.1 ml (at least about $250 \times 10^3$ cells/ml in complete medium) of cell suspension (as above) in complete medium was pipetted over the emulsion. The remainder of the volume of the well was filled with complete culture medium to provide a total volume of about 0.4 ml in the well.

After each desired period of incubation, the extent of cell growth was readily determined by withdrawing a small amount of the inoculated emulsion and observing the droplets using phase contrast microscopy.

By the process of this invention large quantities of cells can very simply and efficiently be harvested. All that is required is to break the emulsion, as by centrifugation, whereupon the cells collect at the interface developed between the culture medium and the disperse phase (e.g. the fluorinated hydrocarbon). Centrifuge forces as high as 6000 times gravity have been used. Centrifugal forces of this magnitude normally break the emulsion in a matter of a few seconds. The cells, clearly visible at the phase boundary as an opaque mass, are readily removed by pipetting. The viability of these harvested cells is readily demonstrated by transferring some of these cells to a conventional cell culture substrate (e.g. polystyrene treated for cell culture) and supplying complete cell culture medium thereto.

EXAMPLE I

A mixture of a perfluorooctanes (designated L-1041 by 3M Company, St. Paul, Minn.) was combined with various amounts (ranging from 0 to 2000 micrograms/-milliliter in final concentration) of PFBC. An emulsion was formed using a capillary tube having a bore of about 100 microns for introducing the fluorocarbon liquid into the tissue culture medium under a pressure of 3 to 15 psi. These conditions produce droplets of fluorocarbon liquid which are of about 200 microns in diameter. The tissue culture medium was the Dulbecco medium with 10% by volume fetal calf serum. This emulsion was maintained in a gently agitated state while several (usually 3) changes of the tissue culture medium were made. These changes of culture medium ensured that the droplets would be well coated with protein and that the effect of any contaminants in the system would be reduced. The cell culture was conducted in a standard microtiter plate with cylindrical wells. A volume (0.1 ml) of protein-coated fluorocarbon droplets plus culture medium (i.e. the emulsion) was pipetted into a series of wells. Next, 0.1 ml of a suspension of normal diploid human cells, obtained originally from amniocentesis in complete medium was pipetted over the emulsion. The remainder of the volume of each well was filed with complete culture medium to provide a total volume of about 0.4 ml in the well.

To feed the cells, the spent media above the emulsion in each cell was withdrawn and replaced with fresh media approximately every other day. At different times following inoculation, the contants of one of these given wells was withdrawn and the droplets separated from the excess aqueous phase. The cell nuclei were released from the droplets, stained and counted. The cell count is set forth in Table I below in which each value is the average of two individual measurements.

TABLE I

| CONC PFBC | TIME (DAYS) | | | | | |
|---|---|---|---|---|---|---|
| (µg/ml) | 1 | 2 | 3 | 6 | 7 | 8 |
| 0 | 3.0* | 1.9 | 1.7 | 2.8 | 3.4 | 2.8 |
| 8 | 6.1 | 10.5 | 8.6 | 3.4 | 6.5 | 7.5 |
| 31 | 5.6 | 15.0 | 14.8 | 11.2 | 13.8 | 15.0 |
| 125 | 8.0 | 13.8 | 18.7 | 21.5 | 25.1 | 24.9 |
| 500 | 7.7 | 14.8 | 18.1 | 31.6 | 37.0 | 42.4 |
| 2000 | 8.0 | 10.1 | 15.3 | 24.9 | 27.5 | 32.0 |

*NUMBER OF CELLS PER 0.1 ml EMULSION (IN THOUSANDS)

This data illustrated the necessity of using a surface active additive to successfully grow normal human cells on liquid droplets. Also, this general procedure can be used to determine the optimum surface charge density for a given living cell. In this example, it was determined that at 500 µg/ml of additive a droplet having a diameter of about 200 microns is provided with a surface charge density of about 40 charges per square nanometer.

EXAMPLE II

The procedure of Example I was repeated using an additive concentration of 500 µg/ml PFBC dissolved the L-1041 perfluorooctanes. Each well was inoculated with $17 \times 10^3$ MRC-5 cells, which are normal diploid lung fibroblasts. The data set forth below in Table II are indicative of the logarithmic growth of this fibroblast on the liquid microcarriers with a generation time of approximately 24 hours. This is a generation time comparable to that measured on solid substrates for these cells.

TABLE II

| TIME (HR) | # OF CELLS/0.1 ml EMULSION* (IN THOUSANDS) |
|---|---|
| 20 | 18.6 |
| 44 | 24.3 |
| 68 | 61.9 |
| 140 | 175 |
| 164 | 199 |

*AVERAGE OF THREE INDIVIDUAL MEASUREMENTS

The system of this invention is easily optimized for different types of cells, because the surface charge density for a given system is easily controlled and readily reproducible. It is contemplated within the scope of this invention that the term "droplets" can include solid microspheres coated with liquid, the liquid coating being the additive-containing liquid used herein as the disperse phase. The process of this invention enables harvesting by a simple mechanical procedure which avoids the uncertain effects on the cell harvest entailed in conventional use of proteolytic enzymes and/or chelating agents.

Although the description herein includes process steps for separating the cells from the droplets and recovering the cells so separated, these steps may not be employed. Thus, for example, the object may be to grow the cells and keep them alive on the droplets, while collecting some desired product secreted by the cells. Another desired end may be to recover a product manufactured by the cells while attached to the droplets, but not secreted, in which case the cells may be ruptured in place to obtain such product.

What we claim as new and desire to secure by Letters Patent of the United States is:

1. The method of growing cells in tissue culture medium wherein the cells attach, spread and divide comprising the steps of
  (a) preparing a heterogeneous system in which a first liquid is dispersed in the form of a large number of small droplets in a second liquid; said second liquid being a sterile, aqueous tissue culture medium containing proteins; said first liquid being non-toxic to living cells, being relatively immiscible with said second liquid and containing sufficient surface active polar additive previously dissolved therein to electrically charge the surface of said droplets to a charge density in excess of about 10 charges per square nanometer whereby proteins from said culture medium coat said droplets;
  (b) bringing living cells into contact with said protein-coated droplets; and
  (c) permitting sufficient time to elapse with suitable conditions of temperature, pH, carbon dioxide concentration and oxygen tension prevailing in said system for cell growth to occur over said protein-coated droplets.

2. The method recited in claim 1 wherein the liquid disperse phase is at least one fluorocarbon liquid.

3. The method recited in claim 1 wherein the surface active polar additive is an acid chloride.

4. The method recited in claim 1 wherein the additive is pentafluorobenzoyl chloride and the droplets are about 200 microns in diameter.

5. The method recited in claim 2 wherein the electrical charge is negative and the concentration of surface active polar additive in the first liquid is in the range of from about 100 to about 1000 micrograms per milliliter.

6. The method recited in claim 5 wherein the additive is pentafluorobenzoyl chloride and the concentration in the fluorocarbon is about 500 micrograms per milliliter.

7. The method recited in claim 1 wherein the living cells are normal human fibroblasts.

8. The method recited in claim 1 wherein the charge density is in the range of from about 10 to about 100 charges per square nanometer.

9. The method recited in claim 1 wherein the additional steps are employed of:
  (d) separating cells from the droplets and
  (e) recovering said separated cells.

10. The method of growing cells in tissue culture medium comprising the steps of:
  (a) subjecting a liquid fluorocarbon to sonication in a first liquid selected from the group consisting of water and ethylene glycol;
  (b) separating the fluorocarbon from said first liquid;
  (c) preparing an emulsion in which the sonicated fluorocarbon is dispersed in the form of a large number of small droplets in a second liquid; said second liquid being a sterile, aqueous tissue culture medium containing proteins; said droplets having charge densities in excess of about 10 charges per square nanometer whereby proteins from said culture medium coat said droplets;
  (d) bringing living cells into contact with said protein-coated droplets; and
  (e) permitting sufficient time to elapse with suitable conditions of temperature, pH, carbon dioxide concentration and oxygen tension prevailing in said system for cell growth to occur over said protein-coated droplets.

11. The method recited in claim 10 wherein the charge density is in the range of from about 10 to about 100 charges per square nanometer.

12. The method recited in claim 10 wherein the additional steps are employed of:
  (d) separating cells from the droplets and
  (e) recovering said separated cells.

* * * * *

UNITED STATES PATENT AND TRADEMARK OFFICE
CERTIFICATE OF CORRECTION

PATENT NO. : 4,514,500

DATED : April 30, 1985

INVENTOR(S) : Ivar Giaever and Charles R. Keese

It is certified that error appears in the above-identified patent and that said Letters Patent is hereby corrected as shown below:

On the face sheet of the patent in the inventor designation the name "Richard C. Keese" should read -Charles R. Keese-;

On the face sheet the assignment designation should be changed to read: Assors of part interest each to General Electric Company a corp. of N. Y. International Foundation for Cancer Research, a corp of MD.

Signed and Sealed this

Seventeenth Day of December 1985

[SEAL]

Attest:

DONALD J. QUIGG

Attesting Officer

Commissioner of Patents and Trademarks